United States Patent [19]

Raitto

[11] 4,372,325
[45] Feb. 8, 1983

[54] METHOD FOR TAKING A BLOOD SAMPLE

[75] Inventor: Russell G. Raitto, Fitzwilliam, N.H.

[73] Assignee: Concord Laboratories, Inc., Keene, N.H.

[21] Appl. No.: 317,307

[22] Filed: Nov. 2, 1981

Related U.S. Application Data

[60] Division of Ser. No. 870,118, Jan. 17, 1978, which is a continuation-in-part of Ser. No. 714,644, Aug. 16, 1976, abandoned.

[51] Int. Cl.³ ............................................. A61B 5/14
[52] U.S. Cl. .................................................... 128/763
[58] Field of Search ............................. 128/760–766, 128/218 R, 218 P, 218 PA, 234, 276

[56] References Cited

U.S. PATENT DOCUMENTS

| | | | |
|---|---|---|---|
| 1,165,686 | 12/1915 | McElroy | 128/234 |
| 1,948,982 | 2/1934 | Cutter | 128/218 |
| 2,419,401 | 2/1946 | Hinds | 128/218 |
| 3,147,753 | 9/1964 | Nogier et al. | 128/218 |
| 3,809,056 | 6/1975 | Moorehead | 128/218 |
| 3,930,492 | 1/1976 | Hatsuno | 128/DIG. 5 |
| 4,041,934 | 8/1977 | Genese | 128/DIG. 5 |

FOREIGN PATENT DOCUMENTS

| | | |
|---|---|---|
| 228538 | of 0000 | Australia . |
| 2261631 | of 0000 | Fed. Rep. of Germany . |
| 78213 | of 0000 | France . |
| 1228933 | of 0000 | France . |
| 1500009 | of 0000 | France . |
| 202402 | of 0000 | Sweden . |

*Primary Examiner*—John D. Yasko
*Attorney, Agent, or Firm*—Sewall P. Bronstein; George W. Neuner

[57] ABSTRACT

An improved method for taking a sample of blood using a disposable syringe and hypodermic needle assembly comprising the steps of moving the plunger tip of the syringe axially forwardly to expel liquid anti-coagulant and air from the syringe barrel until initial contact of the tip with the barrel end is made, whereby a predetermined amount of the anti-coagulant remains in the barrel; followed by inserting the needle into a blood vessel of the patient and permitting the blood pressure in the blood vessel to move the plunger tip and plunger axially rearwardly in the barrel to take a sample of blood.

1 Claim, 12 Drawing Figures

METHOD FOR TAKING A BLOOD SAMPLE

This is a division of application Ser. No. 870,118 filed Jan. 17, 1978 which is continuation in part of 714,644 filed Aug. 16, 1976 now abandoned.

BACKGROUND OF THE INVENTION

This invention relates generally to a hypodermic syringe for obtaining a sample of a body fluid, more particularly for drawing samples from the patient's artery or vein for blood gas analysis or other testing, and for administering fluids, more particularly for administering epidural anaesthesia.

Various syringes and methods for taking blood samples from patients are known. Such samples are normally taken by means of a syringe which includes a generally cylindrical syringe barrel having a plunger therein which, when pulled axially by an operator, creates a suction force drawing blood into the barrel through a hypodermic needle. Many tests are performed on the blood which is thus obtained from the vein of the patient. However, an increasingly important method of determining the medical status of a patient is the obtaining of arterial blood samples for testing the blood for its content of various gases. Such samples are tested for the partial pressure of oxygen, the partial pressure of carbon dioxide, the ph of the blood, the electrolyte balance, and various other tests known in the art.

Syringes previously used in obtaining arterial blood samples have generally been glass syringes, in which the cylindrical barrel is made of glass and the plunger is a ground glass rod which closely fits within the cylinder. Generally the technique for taking samples with such devices comprises, as a first step, the drawing of an anticoagulant solution, such as sodium heparin, into the syringe to replace the air in the syringe. This solution also acts as a lubricant for the walls so that the glass plunger may move relatively freely within the cylinder. The syringe is inverted and all air is expelled from the barrel and needle, along with the bulk of the anti-coagulant solution, which is normally far in excess of the amount needed for the blood sample. It is extremely important that all air be expelled from the syringe, since one of the tests performed is the measurement of the amount of oxygen present in the blood, and even minute contamination with air will prevent accurate measurement of that amount. After suitable preparation of the patient, the hypodermic needle is inserted into the artery and blood is either forced into the syringe by the pressure of the blood in the artery or is drawn into the syringe barrel by withdrawing the plunger. One advantage of the glass syringe previously used is the ease with which the plunger may be moved within the lubricated barrel. The glass plunger is ground to very close tolerances, so that it is sufficiently close to the syringe barrel wall to prevent leakage but sufficiently far away to allow formation of a thin film of the anticoagulant. Even very low arterial blood pressures are usually sufficient to enter the syringe and force the glass plunger backwards without any aid from the person taking the sample. Upon entry into the syringe the blood mixes with whatever anticoagulant solution remains in the needle, syringe tip and syringe barrel after the excess has been expelled.

Glass syringes are also conventionally used in epidural anaesthesia employing the loss of resistance technique because of the low resistance to movement of the plunger in the barrel. Such technique involves loading the syringe with 2-3 ml of normal saline, sterile distilled water or air. The needle (usually 16-18 g) is then applied to the syringe. The needle is then inserted into the back towards the spinal area in question, all the while exerting gentle pressure on the plunger. When the needle tip goes through the ligamenta flava into the potential epidural space, the loss of resistance will be immediately felt by the thumb because the fluid or air will be pushed into the space. Thereafter the syringe is removed from the inserted needle and is replaced on the needle by a syringe loaded with anaethesia. This "loss of resistance" technique requires a syringe with an exceedingly smooth action and low resistance.

The glass syringes previously used have suffered from a number of disadvantages. They are expensive since the grinding requires close tolerances, in the order of 0.0007 inches clearance between the piston and the cylindrical syringe body. They are easily breakable, which is especially costly after the sample has been taken. The glass plunger and the glass barrel of each syringe must commonly be matched during the grinding by the manufacturer, since variations in grinding from one plunger to another may be sufficient to permit leakage of air or other material around the plunger, which will contaminate the sample. Thus the barrels and plungers cannot easily be individually mass produced since the plungers often cannot be satisfactorily interchanged one with another in any given barrel, as pointed out in U.S. Pat. No. 2,419,201 to Hinds. Further, because of the easy movement of the glass plunger in the cylinder, the plunger falls out of the barrel of its own weight, and normally breaks on the floor, unless the syringe is carried needle end down. Special metal holders for the glass barrel have been used to prevent this problem.

Attempts have been made to avoid these disadvantages by either manufacturing both the barrel and the plunger out of materials other than glass, such as plastics, or by using glass barrels with plastic plungers. In order to prevent leakage around the plunger, these syringes depend upon the use of a compressible and elastomeric tip at the end of the plunger, which tip generally has one or more ribs which are slightly larger in diameter than the inside of the barrel in their uncompressed state and which, when placed within the barrel, are deformed and compressed against the interior wall of the barrel and thereby form a seal. This type of seal, however, has made the movement of the plunger within the barrel difficult, thus normally requiring manual withdrawal of the plunger to obtain the blood sample, particularly when the patient's arterial pressure is low as is often the case. The handling of the syringe which is involved when manual withdrawal of the plunger is required may cause traumatization or collapse of the artery from which the blood is being taken. A further major problem has been the fact that when an axial force is applied to the plunger to expel the air and excess anticoagulant solution, the compressible elastomeric tip at the end of the plunger compresses and deforms against the floor of the syringe barrel. The initial contact of the compressible and elastomeric tip with the barrel floor is at an area spaced from the central needle opening in the floor. As force continues to be applied after initial contact the tip is compressed and deformed against the floor to move the contact area radially inwardly toward the needle opening. When the plunger is released prior to the insertion of the hypodermic needle into the artery, the pressure on the compressible and elastomeric tip is also released whereby it recovers its normal shape and in so doing moves back slightly from the barrel floor until its only contact with such floor is its initial contact area thereby drawing a small amount of air into the tip of the hypodermic needle which becomes mixed with the blood sample thereby increasing its oxygen and nitrogen content. Also, air bubbles tend to collect on the forward face of the elastomeric tip particularly at the area immediately adjacent the point of contact with the syringe barrel wall. Since the samples which are drawn to test for the amount of oxygen and carbon dioxide in the blood are very small, e.g., 2, 5 or 10 ml, even minute amounts of oxygen and carbon dioxide leaked into the sample or in the form of air bubbles have potentially adverse effects on the results obtained. The compressibility of the plunger tip also cause non-uniformity in the amount of anticoagulant left in the syringe barrel, syringe tip and hypodermic needle. As can be readily appreciated, the amount left will depend upon the amount of pressure used to expel the air and excess anticoagulant since greater pressure will compress and distort the compressible plunger tip to a greater degree, thus expelling more anticoagulant. If too little anticoagulant solution remains to be mixed with the blood, the blood may coagulate prior to testing and thus adversely affect the results obtained. If, on the other hand, too much anticoagulant solution is left in the syringe, its presence may adversely affect the test, as is known in the art.

OBJECTS OF THE INVENTION

Accordingly, an object of the present invention is to provide a simple, inexpensive syringe with compressible and elastomeric plunger tip, particularly one suitable for taking arterial blood samples and epidural anaesthesia, which avoids the difficulties previously encountered with the glass syringes but which also avoids the aforesaid difficulties previously encountered with syringes employing such tips. Thus, the syringe of the present invention, although employing an elastomeric and compressible plunger tip, avoids air contamination of the sample which will interfere with the results obtained. It is a further object of the invention to provide such a syringe which is adapted to prevent air being sucked into the hypodermic needle when the plunger is released prior to taking the sample and to reduce the collection of air bubbles on the elastomeric tip surface. It is a further object of the invention to provide such a syringe which is adapted so as to supply a uniform and correct amount of anticoagulant solution to the blood sample being taken. It is a further object to provide such a syringe in which the plunger is more easily movable in the syringe barrel than conventional plungers with elastomeric tip. In fact, the ease with which the plunger can be moved approaches, and, in some cases, equals the ease with which conventional glass plungers can be moved so that it responds to very low arterial pressures and hence minimizes the possibility of traumatization of the patient. On the other hand, an excellent uniform seal is provided between the elastomeric tip and the syringe barrel throughout the distance travelled by the tip to obtain the sample. It is a still further object to provide such a syringe which limits the amount of sample taken to a precise, predetermined amount. It is a further object to avoid any adverse effect on the seal between plunger tip and barrel by cantering or bowing of the plunger stem. It is a further object to provide a syringe having all of these advantages which is simple and inexpensive to manufacture, and thus of low cost and extremely simple to operate in a manner which gives uniform and accurate results.

Other objects and advantages of the present invention will be apparent from the following description and accompanying drawings.

SUMMARY OF THE INVENTION

Certain of the aforesaid objects and advantages are achieved in accordance with the present invention by providing a syringe in which the compressible elastomeric tip of the plunger is provided with a peripheral annular wiper lip extending axially forwardly toward the floor of the syringe barrel and radially outwardly at an acute angle to the longitudinal center line of the barrel and plunger. The normal outer diameter of the wiper, i.e., the wiper edge, is slightly greater than the inner diameter of the syringe barrel. By virtue of the fact that the wiper extends at an acute angle to the longitudinal center line of the barrel and plunger it tends to be forced to rock radially inwardly about its base (where it is joined to the main part of the plunger tip) against the resilient resistance offered by the elastomeric material when forced into the syringe barrel, whereby the wiper edge is yieldably pressed against the inner wall of the barrel to form an effective seal therebetween which increases in effect with increase in the force tending to move the plunger axially.

Although the seal achieved is excellent, the wiper edge is only lightly pressed against the barrel surface so that the plunger responds to lower pressures as compared to conventional plastic syringes. Accordingly, the syringe fills automatically by even very low arterial pressures with no need for manually withdrawing the plunger and is very sensitive to the touch which makes it highly satisfactory for epidural anaesthesia employing the loss of resistance technique.

Another aspect of the invention involves designing the forward end portion of the plunger tip so that when the plunger is moved to its forwardmost position against the barrel floor, e.g., to eject air and excess liquid anticoagulant before taking a sample, the initial contact of the elastomeric and compressible tip with the barrel floor is at the area of the floor immediately adjacent the needle opening in the floor to form a seal between the tip and such area. This prevents the further flow of liquid out of the barrel and needle opening and thereby traps a predetermined and uniform desired (sufficient to prevent coagulation but not so much as to interfere with the tests) amount of the liquid anti-coagulant in a sealed space or chamber of predetermined volume remaining between the tip and the barrel floor. The trapped noncompressible liquid acts as a stop and barrier to prevent deformation and compression of the tip into further contact with the barrel floor upon continued application of forward force on the plunger, i.e., it prevents the spread of the contact area by the continued application of the force. Accordingly, when the force on the plunger is released air intake is minimized by recovery of the compressible and elastomeric tip back to its initial-contact shape.

Preferably the aforesaid space or chamber between the tip and floor is formed by an annular trough in the end face of the tip formed on one side by the wiper and on the other side by a centrally located reduced end portion of the tip extending axially forwardly from the base of the wiper. It is this end portion which forms the seal with the barrel floor immediately adjacent the needle opening. Preferably the end face of such end portion is convex in shape but it can be of any shape (preferably tapered inwardly as it extends forwardly) which will seal the needle opening on initial contact of the tip with the barrel floor while leaving a space to trap the liquid anti-coagulant, e.g., it may be conical or frusto-conical in shape.

Air intake is further minimized by concentrating and substantially restricting force applied by the plunger stem to the compressible and elastomeric plunger tip in the forward direction after the aforesaid initial contact, at and to that portion of the tip which is behind the space and liquid trapped therein with a minimum of force (desirably zero) being applied to the portion of the tip member located behind the needle opening, whereby after the aforesaid initial contact distortion of the tip member into such opening is minimized. This is preferably achieved by providing lost forward axial motion of the plunger stem relative to the portion of the tip behind the needle opening, but not relative to the portion of the tip behind the trapped liquid, upon continued application of axial forward force to the stem after initial contact between tip and barrel floor. In this way, such continued force is concentrated at and restricted to the portion of the tip behind the trapped noncompressible liquid to compress such portion between the liquid and the stem and is not applied to the portion of the tip behind the needle opening.

In another aspect of the invention, means is provided for minimizing the risk of leakage due to cantering of the annular wiper edge relative to the barrel wall, with consequent reduction in sealing pressure between such edge and such wall, due to cantering of the plunger stem by the operator during operation or due to a warped or bowed or otherwise defective plunger stem. Preferably this is achieved by attaching the stem to the tip to permit radial play therebetween, i.e., by the use of a loose radial fit.

In yet another aspect of the invention, by virtue of the reduction in diameter of the aforesaid reduced leading end portion of the plunger tip as compared to the portion of the tip which trails such end portion, as well as the wiper, the solid wall thickness of the tip over most of its length and to which axial forward force is applied lies behind the trough to strengthen the tip.

In yet another aspect of the invention, the wiper is tapered in thickness so that it is wider at its base than at its wiping edge. The wider base strengthens the wiper leaving the thinner edge portion flexible to apply only a gentle sealing pressure to the wall of the barrel.

In yet another aspect of the invention at least the portion of the syringe barrel traversed by the plunger tip, in taking a sample or employing the "loss of resistance" technique in epidural anesthesia, has a constant inside cylindrical diameter, i.e., the inside wall of the barrel does not taper inwardly or outwardly. This keeps the light sealing pressure of the wiper on the barrel wall uniform over its operative range of travel in the barrel.

In yet another aspect of the invention the barrel wall is provided with a stop which prevents rearward axial movement, by arterial pressure, of the plunger tip beyond the point where the desired blood sample size has been obtained. Although the stop offers sufficient resistance to prevent movement of the tip beyond it by virtue of arterial pressure, such resistance is insufficient to prevent the plunger tip from being pulled out of and pushed into the barrel by hand. The stop also offers sufficient resistance to prevent the plunger from falling out of the barrel by force of gravity when the syringe is inverted.

THE DRAWINGS

For a better understanding of the invention, reference is made to the following detailed description to be read in conjunction with the accompanying drawings, in which FIG. 1 is a longitudinal section of the inward or forward part of a commercial prior art blood sampling syringe with compressible and elastomeric plunger tip showing in full lines the initial contact position of the tip with the barrel floor and in broken lines the position of the tip following initial contact upon continued inward or forward force applied to the plunger;

DETAILED DESCRIPTION

Figure 1:
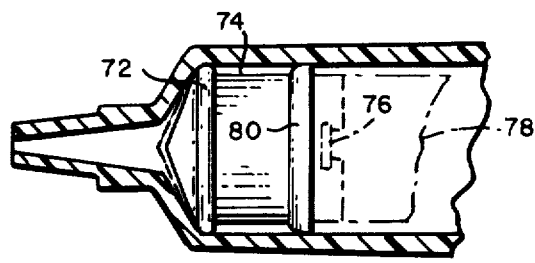
Figure 2:
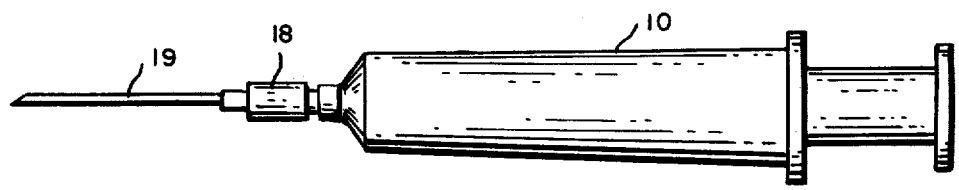
FIG. 2 is a planar side view of a preferred embodiment of the syringe of the present invention.

Referring to the Figures of the drawings, the syringe depicted has a relatively rigid, generally cylindrical hollow body or barrel 10, preferably made of an inexpensive substantially transparent plastic material, such as polyethylene or polypropylene, which is inert to, i.e., does not affect, the sample to be taken, and which is substantially impermeable to oxygen and carbon dioxide. Other suitable materials, such as polystyrenes, acrylic or methacrylic polymers and various glasses, are well known in the art. The cylindrical barrel has a central bore 36 and terminates at one end with finger piece 10a. This finger piece 10a generally has the shape of an annular flange but can be any shape which provides support for two fingers, e.g., hexagonal, or take the form of two tabs. The barrel terminates at the other end in an axially forwardly and radially inwardly tapered end wall 20 which forms the tapered floor 21 of the bore 36 and which extends forwardly into the reduced diameter tapered tip 16 of the barrel. As shown, barrel tip 16 is generally frusto-conical in shape. Tip 16 is shown as carrying the hypodermic needle 19 through frictional engagement of the tapered periphery thereof with the tapered end of the internal passage of cylindrical base member 18 of the needle 19. However, the needle may be secured to the tip 16 by a conventional luer lock arrangement on the base member 18 and tip 16. The barrel floor 21 and end wall 20 have a centrally located needle opening 22 therein which extends into the internal passage 47 of tip 16.

Figure 3:
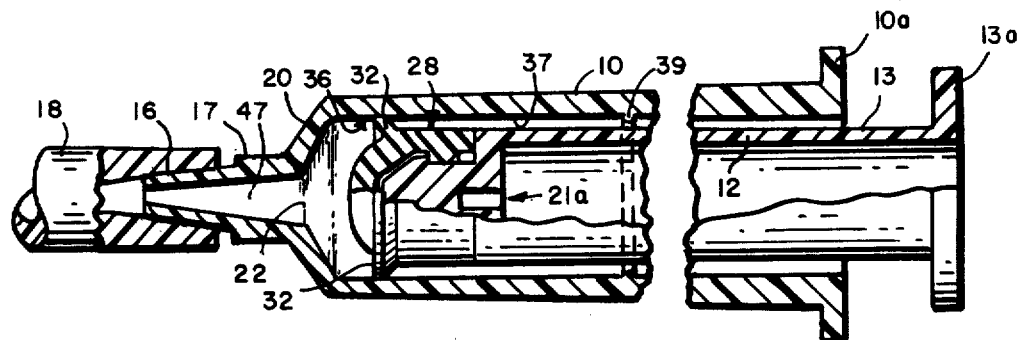
FIG. 3 is a longitudinal section of the syringe of FIG. 1 with the compressible and elastomeric tip in a position intermediate its limits of travel.
Figure 4:
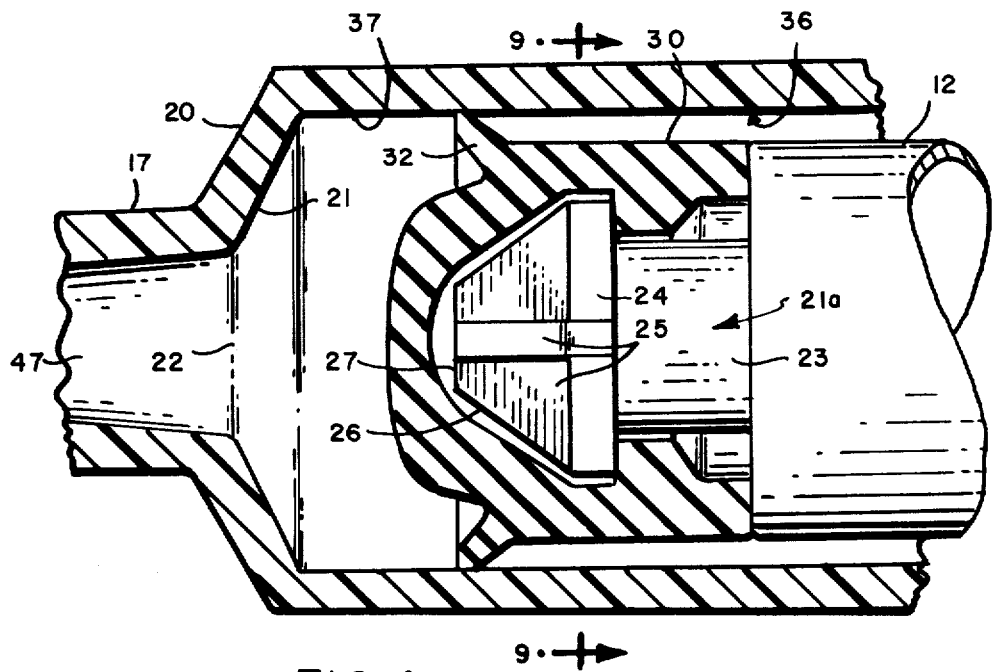
FIG. 4 is an enlarged view of the forward portion of the syringe of FIG. 3.

In a preferred embodiment, the wall of bore 36 of the barrel 10 is cylindrical and non-tapered in at least the working area 37 thereof, i.e., the area of the cylinder which is traversed by the compressible and elastomeric plunger tip 28 in taking the sample. Thus, as shown in FIG. 3, the inner side wall (bore) of the barrel is straight (cylindrical) in the longitudinal direction and there is no convergence or divergence at the area 37 between the end wall 20 and annular rib 39, which extends radially inwardly from the inner side wall of bore 36 and the purpose of which will be described hereinafter. The portion of the inner side wall of bore 36 of the barrel rearward of the rib 39 may be tapered slightly outwardly as it extends rearwardly to aid in molding the barrel but it need not be.

The syringe also comprises a hollow cylindrical plunger 12 having a relatively rigid plunger stem 13 and a compressible and elastomeric plunger tip 28.

The plunger stem 13 is preferably made of an inexpensive plastic material, such as polyethylene or polypropylene, which is also inert to the sample to be taken. Other materials which can be used are the same materials of which the barrel is made. In fact, the plunger stem is preferably made of the same material as the barrel but it need not be. At its rearward end, stem 13 terminates in a thumb supporting flange 13a. THe plunger stem terminates at the other end in a head portion 12a (FIG. 5) to which the compressible and elastomeric plunger tip 28 is secured. Head portion 21a comprises a hollow reduced diameter cylindrical neck portion 23 forming a shoulder 31 with the main part of the plunger stem. Neck portion 23 extends axially in a forward direction into square shaped plate portion 24 which forms a shoulder 45 with portion 23 and from which in turn there extends axially in a forward direction a plurality of radially extending fins 25, the peripheral edges of which are tapered radially inwardly at 26 as shown and the forward edges of which are flattened at 27. Fins 25 run diagonally from opposite corners of the plate portion 24 through the center thereof.

Figure 8:
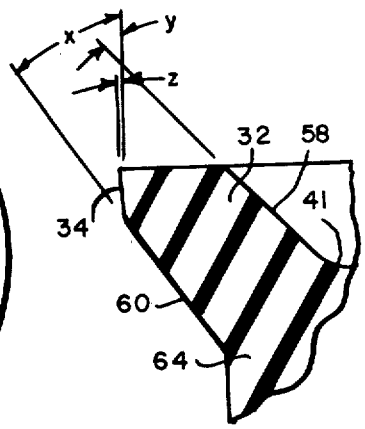
FIG. 8 is an enlarged view in section of a part (rotated so that the longitudinal axis is oriented vertically in the illustration) of the wiper of the plunger tip of FIG. 4 before it is inserted into the syringe barrel.
Figure 9:
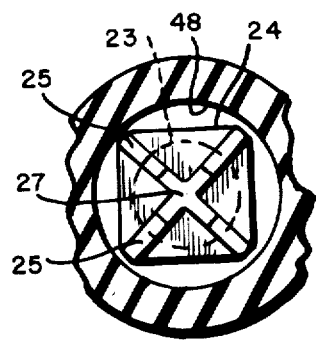
FIG. 9 is a section taken along the line 9—9 of FIG. 4.

The hollow compressible and elastomeric plunger tip 28 is made up of a main hollow cylindrical portion 30 from the periphery of the forward portion of which extends axially forwardly (axially forwardly and axially inwardly mean toward the barrel floor whereas axially rearwardly and axially outwardly mean away from the barrel floor) and radially outwardly at an acute angle y (see FIGS. 5, 6 and 8) from the longitudinal center axis of the plunger and plunger tip, an annular wiper lip 32, the wiping edge 34 of which is resiliently and yieldably forced into sealing engagement with the inner bore or wall 37 of the barrel. The plunger tip extends axially forwardly from the base 64 of wiper 32 into a reduced diameter leading end portion 38, the base 43 of which has an outside frusto-conical shaped taper which terminates in a convex curvilinear end face 43a. An annular recess or trough 41 is formed by the axially forward and radially inner surface 58 of the annular wiper 32 and the radially outer surface 43 of the end portion 38, as shown.

The rearward end 56 of plunger tip 28 has an internal socket 42 in which is received the head 21a of the plunger stem 12 to secure the plunger tip to the end of the plunger stem. Socket 42 has an enlarged rear cylindrical end portion 44 which extends forwardly into a reduced cylindrical portion 46 which then extends forwardly into an enlarged diameter cylindrical portion 48 (same diameter as 44) which forms a shoulder 29 where it meets with portion 46 and which extends forwardly into a radially inwardly tapered frusto-conical shaped portion 50, which in turn extends into a curvilinear concave end portion 52. The taper of socket wall 50 is slightly sharper than that of outer surface 43 and the curve of socket wall 52 is slightly sharper than that of outer surface 43a, as shown.

Preferably, the circle formed where the frusto-conical outer surface 43 of end portion 38 changes into the curvilinear end surface 43a, lies on an imaginary axial extension of cylindrical socket walls 48 and 44.

The cylindrical portion 23 of the head 21a of the plunger stem is located within the rearward portions 44 and 46 of the plunger tip socket and is spaced radially inwardly therefrom as shown. The square shaped plate portion 24 of the plunger stem is located within the enlarged cylindrical portion 48 of the plunger tip socket and is spaced radially inwardly therefrom as shown. The fins 25 of the plunger stem head are located within the tapered portion 50 of the socket and are spaced radially inwardly therefrom and the ends thereof are spaced axially rearward from the end wall 52 of the socket, all as shown. The annular end 56 of the plunger tip is held in secure engagement with the shoulder 31 of the plunger stem and the shoulder 29 of the socket is held in secure engagement with the shoulder 45 of the plunger stem head to thereby firmly secure the plunger tip on the end of the plunger stem 13.

The only part of the plunger which engages the inner wall of the barrel is the annular wiping edge 34 which exerts only a slight force on such wall to thereby reduce frictional drag and permit the plunger to be easily moved axially in the barrel.

The acute angle y between the forward or leading wiper surface 58 (FIG. 8) of the wiper 32 and the longitudinal center axis of the plunger tip is slightly greater than the acute angle x between the rearward or trailing wiper surface 60 of the wiper and the longitudinal center axis whereby the wiper is tapered in thickness with the base 64 of the wiper being thicker than the end portion of the wiper. The thicker base strengthens the wiper whereas the tapered thinner end portion increases the flexibility of the wiper edge to provide only gentle sealing pressure on the inner barrel wall to thereby minimize resistance to axial movement of the plunger.

In its relaxed state when the plunger tip is removed from the barrel, the wiper edge 34 of the wiper is of slightly greater diameter than the inner bore 37 of the barrel so that when the plunger tip is forced into the bore such edge 34 is forced radially inwardly about the base 64 of the wiper i.e., the wiper is bent or rocked radially inwardly about its base, against the force exerted by the elastic and compressible material, which force yieldably and with only a slight pressure urges such wiper edge into excellent sealing engagement with the bore wall 37 with very little frictional drag.

In its relaxed state when the plunger tip is removed from the barrel, the wiper edge surface 34 preferably extends radially outwardly and axially forwardly at a slight angle z, e.g., about 2° to the longitudinal center axis of the plunger tip and the barrel bore. The purpose of this is to reduce the chance of leakage while still achieving gentle sealing pressure. When the plunger tip is forced into the barrel bore, this wiper edge surface 34 is forced to assume a position in which it is parallel to the longitudinal axis of the plunger tip and barrel bore. Without this slight inclination of the wiper edge surface 34, the undersized barrel may tend to bend the leading end of such wiper edge surface radially inwardly to either reduce the pressure of the wiper edge surface on the bore wall at such leading end or to cause such leading end to move slightly away from the bore wall to provide a slight space or groove therebetween which may result in leakage. The force of the liquid blood sample shown by the arrows in FIG. 5 tends to aggravate this since it tends to work into any space or decreased pressure area between such leading end and the barrel bore to force such leading end further away from the bore wall with resulting leakage.

By providing this slight angle to the wiper edge surface 34, maximum sealing pressure is applied and concentrated at the leading end of surface 34 where it does the most good and over a relatively small area, thereby minimizing frictional drag.

The plunger tip can be made of any elastomeric and compressible material with memory, which has a low coefficient of friction with the barrel wall material and which is inert to the sample material, to the anti-coagulant and to any other substance which is to be located within the syringe barrel. Natural and synthetic rubbers can be used such as neoprene rubber as well as other elastomeric polymers such as polyvinyl chloride, polyurethanes, polyesters, etc. A preferred material is silicone rubber.

Figure 6:
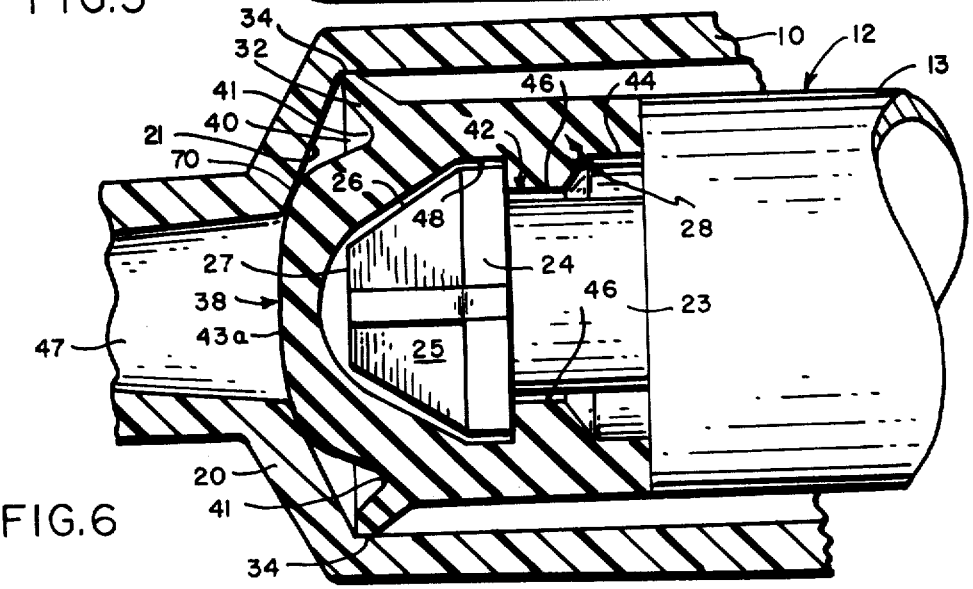
FIG. 6 is a view like FIG. 4, showing the initial contact position of the plunger tip and barrel floor wherein the needle opening is sealed.
Figure 7:
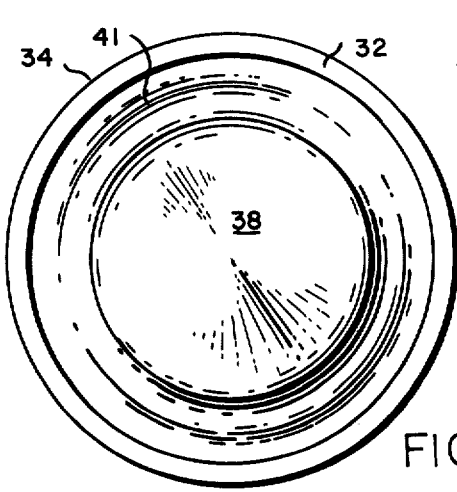
FIG. 7 is an inner end view of the plunger tip of FIG. 4.

It will be noted that the forward end of the plunger tip is so designed that when the plunger tip is moved to its forwardmost position as shown in FIG. 6, the initial contact of the plunger tip with the barrel floor is between the narrow annular area 70 of the barrel floor 21 immediately adjacent the needle opening 22 and the peripheral part of the curved end surface 43a of the end portion 38 of the plunger tip to thereby seal the needle opening 22 against further flow of fluid out of the syringe through the needle opening. At this time the wiper edge 34 reaches the end of the cylindrical bore wall 37 and the trough 41 of the wiper forms with the barrel floor 21 a sealed space or chamber 40 of predetermined size, i.e., sealed by the seal between the plunger tip and the barrel floor at 70 and the seal between the tip and the barrel bore at 34. Note that the difference in taper of the outer and inner surfaces 43 and 50 of the plunger tip increases the wall thickness of the tip behind the seal area 70.

Conventionally in taking a blood sample, a liquid anti-coagulant, e.g., sodium heparin, to prevent coagulation of the blood sample is either drawn into the syringe before the blood sample is taken or is located in the syringe as packaged. The excess of such liquid anti-coagulant and any air is the syringe is then expelled through the needle opening and needle by forward movement of the plunger and plunger tip.

In accordance with the present invention, the excess anti-coagulant and air are expelled by moving the plunger tip to its forwardmost position as shown in FIG. 6. The initial sealing contact between the narrow annular area 70 of the barrel floor immediately adjacent the needle opening and the convex end surface 43a of end portion 38 seals the syringe barrel against further flow of the liquid anti-coagulant out of the syringe and a predetermined amount of the anti-coagulant is thereby trapped in the annular space 40. The size of the trough 41 is such that the anount of anti-coagulant trapped in this space, together with that filling passage 47 and the needle when the plunger tip is in the position shown in FIG. 6, is sufficient to prevent coagulation of the sample taken but is less than an amount which will interfere with the testing of the sample. Accordingly, the right amount of anti-coagulant is automatically assured.

Preferably the volume of the space 40, together with passage 47 and the needle bore, is between 0.01 and 1.0 milliliters and more preferably between 0.25 and 0.5 milliliters for every 5 milliliter of blood sample taken.

The non-compressible liquid trapped in space 40 acts as a non-yieldable stop or barrier to prevent any deformation and compression of the plunger tip against the barrel floor radially outwardly of the narrow annular sealing area 70 upon continued application of forward axial force on the plunger.

Such continued force by the plunger stem on the plunger tip is concentrated and restricted to the peripheral portion of the plunger tip behind the noncompressible trapped liquid in space 40 through shoulder 31 of the stem and the end surface 56 of the plunger tip to thereby compress such peripheral portion between shoulder 31 and the trapped liquid. Although, such force may be concentrated at and restricted to the portion of the tip behind space 40 and sealing area 70, it is highly preferred that it be concentrated at and restricted to the portion behind space 40. At the same time the axial space between the head 21a of the plunger stem and the end 52 of the socket in the plunger tip provides lost motion between such head and tip, i.e., the head moves axially forwardly with respect to the plunger tip but does not engage the surface 52, which is located behind the needle opening 22. Accordingly, the force applied to the end portion 38 of the plunger tip behind the needle opening 22 is substantially zero so that there is substantially no deformation of such end portion into the needle opening 70. Therefore, once initial contact is made between the plunger tip and the barrel floor, there is substantially no deformation of the end of the plunger tip against the barrel floor or into the needle opening so that when the force of the plunger is released there is substantially no undesirable intake of air into the syringe as compared to a plunger tip of a conventional arterial blood sampling syringe of the type shown in FIG. 1 (a plastic syringe sold under the name JELCO by the Jelco Division of Johnson and Johnson) having one or more sealing ribs 72 extending 90° radially outwardly from the periphery of the plunger tip 74.

Note in FIG. 1 that the end of the plunger tip initially engages the barrel floor at its periphery (full line position) when liquid is expelled therefrom, whereupon continued forward axial force on the plunger causes the end of the tip to be deformed and compressed against the floor radially inwardly with the contact area expanding from the peripheral portion of the floor radially inwardly toward the needle opening (broken line position). When such force is released the plunger tip springs back away from the floor to its full line position and in so doing may suck undesired air into the syringe. Also, in most such conventional syringes the end 76 of the plunger 78 stem exerts axial force on the central portion 80 of the plunger tip to deform the end of the tip into the needle opening, which may draw more air back into the syringe when the force is released.

Also note that in the conventional syringe of FIG. 1 with compressible plunger tip, when the plunger tip is forced into the undersize (compared to the sealing rib or ribs) syringe barrel to deform the edge of the rib or ribs radially inwardly, such deformation is resisted by the entire thickness of the plunger tip wall including the radial height of the rib or ribs. This causes the ribs to be urged against the bore wall with substantial force thereby creating substantial frictional drag as compared to the syringe of the instant invention where the resistance to the deforming force of the undersize barrel is the relatively gentle resistance to bending of the wiper.

Whereas with a 10 cc plastic JELCO syringe and 22 gage needle a force of 64 mm/Hg was required to force the plunger back, the force required to force the plunger back with a syringe of the same size embodying the invention was only 15-18 mm/Hg i.e., only about ¼ of the force was required. Accordingly, the syringe of the instant invention fills automatically with very low arterial pressures without manually pulling the plunger outwardly. With a needle of 22 gage, a syringe embodying the instant invention has been found to be as responsive to hydraulic force as a glass syringe.

Figure 5:
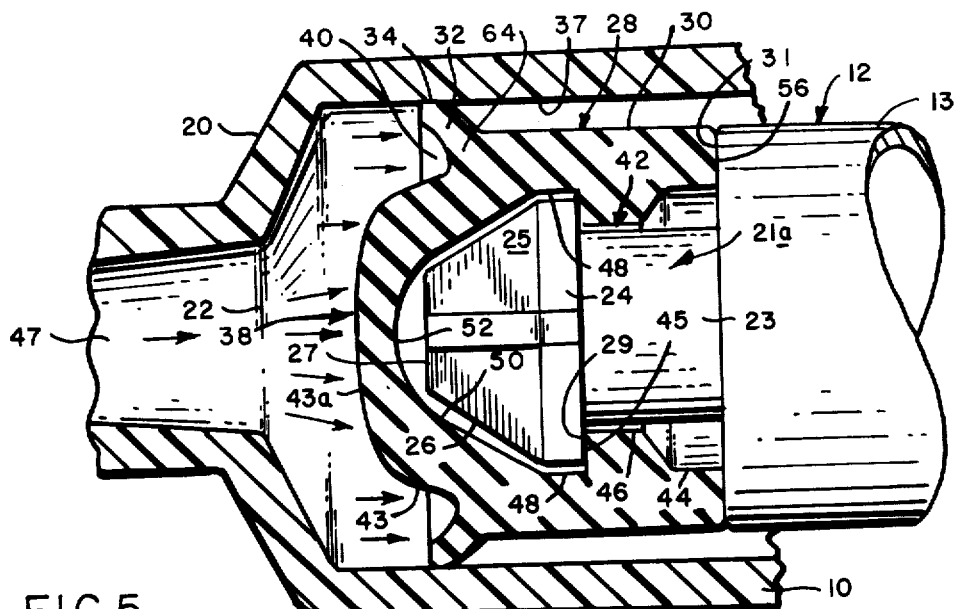
FIG. 5 is a view like FIG. 4 showing how force applied to the tip forces the wiper edge tighter against the barrel wall to increase sealing effect.

In spite of the very low pressure required to fill the syringe of the invention and the very gentle sealing pressure of the wiper edge against the syringe barrel, the sealing achieved is excellent by virtue of the design of the wiper. As seen in FIG. 5, the force shown by the arrows applied by the blood pressure tends to urge the wiping edge against the barrel wall to increase the sealing effect. The plunger tip of the invention has withstood a hydraulic force of 300 mm/Hg without leaking but such large forces are not encountered in use.

Note in FIG. 6 that the trapped liquid in space 40 functions as a non-yieldable support for the portion of the highly flexible and sensitive wiper located radially outwardly as compared to the main portion 30 of the plunger tip to thereby prevent any substantial deformation of such portion upon continued application of forward axial force by the plunger stem after initial contact of the tip with the barrel floor. Also note that because such portion of the wiper lies radially outwardly compared to the wall of main portion 30, to which such continued axial force is applied, very little, if any, such force tends to deform such portion in any event. Also the reactive force of the trapped liquid on the wiper tends to force it into greater sealing engagement with the barrel bore.

The loose circumferential fit between the head 21a of the plunger and the socket 42 of the plunger tip, together with the loose axial fit in the forward direction, prevents cantering of a part of the wiper sealing edge 34 away from the bore by cantering of the plunger by the operator, e.g., by moving the finger piece 13a laterally while operating the syringe, or by virtue of a bowed or warped or uneven plunger. It is difficult to avoid some bowed or warped plungers during manufacture of a lot. Such cantering of a part of the wiper edge away from the bore wall is apt to reduce the sealing pressure applied by such part to thereby cause leakage.

The optimum angle y of the wiper from the longitudinal center axis of the plunger tip and optimum angle z of the wiper edge surface and optimum difference in the angles y and x of the leading and trailing surfaces of the wiper to achieve a thin wiper edge portion and a thicker base depends in part upon the stiffness of the material of the plunger tip.

It has been found that an angle y of 43°, (preferably it varies between about 20° and 65°, more preferably between about 30° and 50°) between the leading surface of the wiper and the longitudinal axis of the plunger tip and an angle x of 35° (preferably the difference over angle y may vary between about 10° and 30°, more preferably between about 4° and 15°) between the trailing surface and the longitudinal axis gives excellent results.

Excellent results have also been achieved with needle sizes of from 20 to 22 gage. The speed with which the plunger tip moves is proportional to the needle gage size.

The rib 39 functions as a stop to limit the outward movement of the plunger tip by engagement of the wiper edge 34 therewith to thereby ensure that a uniform predetermined volume of sample is obtained and also to ensure against the plunger falling out of the barrel.

Although the rib 39 is adequate to resist rearward movement of the plunger due to arterial pressure and due to the weight of the plunger it is inadequate to resist a manual pulling force, which causes deformation of the wiper and consequent movement thereof past the rib to permit the plunger to be inserted and removed from the barrel.

It has been found that air bubbles which in conventional plastic syringes collect at the leading surface of the plunger tip close to the interface of the plunger tip and the barrel bore, do not collect on such surface of the plunger tip of this invention. It is believed that this is due to the particular design of the plunger tip. This is an important advantage since it permits more accurate testing.

The location of the liquid-containing space 40 axially in front of substantially the entire solid axial length of the wall of the plunger tip to which the force is axially applied at 56 greatly strengthens the plunger tip. This is achieved in part by reducing the diameter of the end portion 38 as compared to the main portion of the plunger tip. Although such reduction in diameter strengthens the wiper, it, together with the radially inward taper at 43a, reduces wiper stiffness and thereby increases wiper sensitivity and reduces frictional drag.

Figure 10:
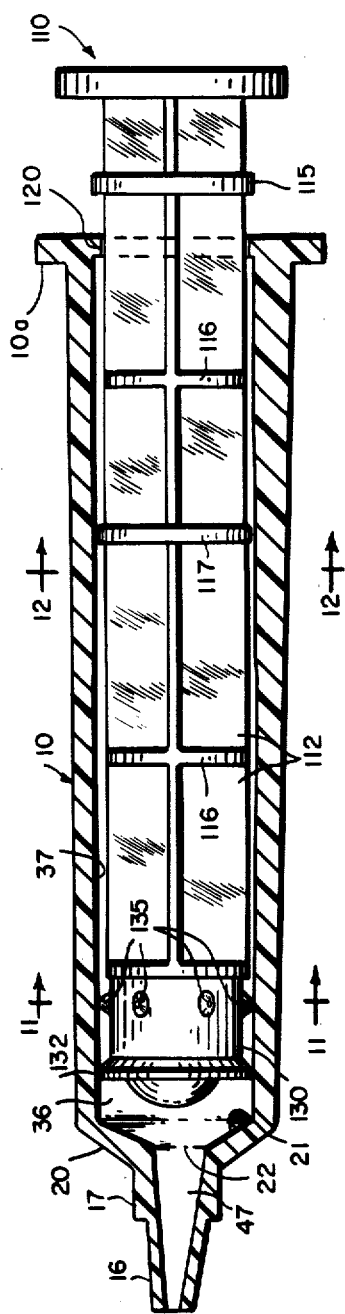
FIG. 10 is a side view of a partial longitudinal section of a preferred embodiment of the syringe of the present invention.
Figure 12:
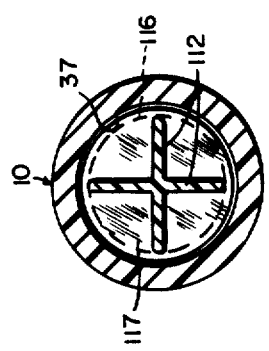
FIG. 12 is a section taken along line 12—12 of FIG. 10.
Figure 11:
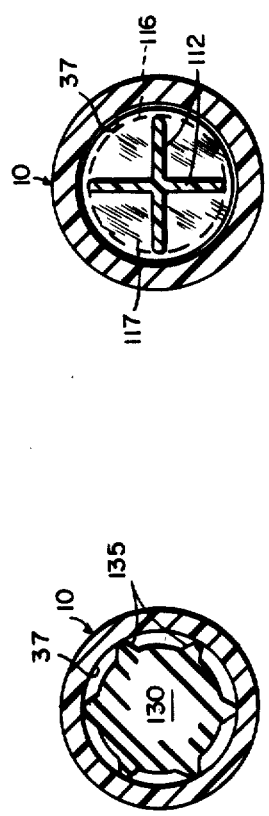
FIG. 11 is a section taken along line 11—11 of FIG. 10.

In another preferred embodiment as illustrated in FIG. 10, the elastomeric plunger tip 130 has a plurality of raised portions 135 spaced around the circumference of the rearward section of the plunger tip 130 and engaging the inner wall 37 with minimum contact to avoid any significant frictional force. These raised portions 135 of the plunger tip 130 prevent canting of the plunger tip to maintain the plunger tip in a concentric position within the syringe barrel 10 and allow the sole wiping edge 132 of the plunger tip to maintain its most effective sealing engagement with the syringe barrel. The raised portions on the rear section of the plunger tip can be of any shape that will accomplish the purpose of preventing canting of the plunger tip. Generally, a semi-spherical, conical, or frusto-conical shape is preferred to avoid excessive frictional contact with the syringe barrel and for ease of manufacture.

The preferred embodiment illustrated in FIG. 10 also shows the plunger 110 having a plunger stem comprising two ribs 112 at right angles to each other and having a number of circular discs 116 with a diameter less than that of the syringe barrel positioned along its axis at right angles to the ribs. One of the discs 117 has a greater diameter than the other discs and functions as a stop to limit outward movement of the plunger by engagement with rib 120 at the end of the syringe barrel when drawing a blood sample. The plunger can be withdrawn from the syringe barrel by exerting additional manual force to move disc 117 past rib 120. The plunger stem also has a disc 115 which is larger in diameter than disc 117 and will not move past rib 120 regardless of the force exerted. Disc 115 functions as a stop preventing further inward movement of the plunger and is positioned to prevent such further inward movement at a predetermined position of said plunger tip to form a chamber or space between the plunger tip 130 and the tapered floor 21 of the bore 36 of the syringe barrel. The size of the chamber or space thus formed can be predetermined to contain a particular quantity of anti-coagulant. Thus disc 115 effects a positive stop preventing further inward movement and avoiding any compression of the plunger tip.

Disc 117 is positioned along the longitudinal axis of the plunger in accord with size of sample to be drawn with the syringe, thus providing an effective preset sample size. Thus the size of the chamber formed by the plunger tip and the floor of the syringe barrel can be sized to contain the precise amount of anti-coagulant required for the sample size.

The aforesaid advantages of the syringe of this invention not only make it highly useful in an improved arterial blood sampling syringe but also for epidural anaesthesia employing the loss of resistance technique and it has been used successfully clinically for that purpose.

While the present syringe is particularly suitable for taking arterial blood samples and for epidural anaesthesia, its suitability for other functions will be readily appreciated in the art. It is disposable and inexpensive. It can be cheaply mass produced out of inexpensive raw materials. There are no breakage problems.

It is not intended that the invention be limited to or by the aforesaid description and accompanying drawings of only one embodiment thereof but only to the subject matter claimed hereinafter and its equivalents.

I claim:

1. A method for taking a sample of blood using a disposable syringe assembly particularly suited because of the low force requirement for the operation thereof to be used for obtaining a blood sample from a patient wherein said syringe comprises a barrel having a cylindrical inner wall and a plunger comprising a plunger stem and a compressible, elastomeric, generally cylindrical plunger tip of lesser diameter than the inner wall of said barrel, said plunger tip having an integral, annular, elastically deformable wiper extending peripherally radially outwardly and axially forwardly from said plunger tip at a forward portion thereof at an acute angle to the longitudinal center axis of said plunger tip and terminating at the outer edge thereof in a wiping edge having a minimal diameter slightly in excess of the diameter of the inner wall of said barrel, thereby forming a sealing engagement with the inner wall of said barrel, said annular wiper being the sole sealing element between said plunger tip and said wall, said plunger being spaced from said barrel along the length thereof so that axial movement between said plunger and said barrel is substantially free of frictional contact except for the contact by said sole sealing element, said syringe having a hypodermic needle attached thereto;

said method comprising moving said plunger tip axially fowardly to expel liquid anti-coagulant and air from said barrel until initial contact of said tip with the barrel end is made, whereby a predetermined amount of said anti-coagulant remains in said barrel; followed by inserting said needle into a blood vessel of a patient and permitting the blood pressure in said blood vessel to move said plunger tip and plunger axially rearwardly in said barrel to take a sample of blood.

* * * * *